(12) United States Patent
Gotoh

(10) Patent No.: US 7,591,587 B2
(45) Date of Patent: Sep. 22, 2009

(54) METHOD FOR CONTROLLING X-RAY DIAGNOSTIC APPARATUS

(75) Inventor: Atsushi Gotoh, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/928,499

(22) Filed: Oct. 30, 2007

(65) Prior Publication Data

US 2008/0056451 A1 Mar. 6, 2008

Related U.S. Application Data

(63) Continuation of application No. PCT/JP2006/314588, filed on Jul. 24, 2006.

(51) Int. Cl.
*H05G 1/02* (2006.01)
*G01N 23/083* (2006.01)

(52) U.S. Cl. .................. 378/196; 378/62; 378/189; 378/197

(58) Field of Classification Search .............. 378/189, 378/196, 197, 198, 62
See application file for complete search history.

(56) References Cited

U.S. PATENT DOCUMENTS

| | | | | |
|---|---|---|---|---|
| 4,674,107 A * | 6/1987 | Urban et al. ................ 378/98 |
| 4,922,512 A * | 5/1990 | Lajus et al. ................ 378/197 |
| 5,159,622 A * | 10/1992 | Sakaniwa et al. .......... 378/196 |
| 5,475,730 A * | 12/1995 | Galando ..................... 378/157 |
| 5,479,470 A * | 12/1995 | Stenfors ..................... 378/196 |
| 5,521,957 A * | 5/1996 | Hansen ....................... 378/198 |
| 6,213,638 B1 * | 4/2001 | Rattner ....................... 378/198 |
| 6,264,364 B1 | 7/2001 | Pflaum et al. |
| 6,309,102 B1 * | 10/2001 | Stenfors ..................... 378/197 |
| 6,315,446 B1 * | 11/2001 | Kidd et al. .................. 378/197 |
| 6,334,708 B1 * | 1/2002 | Kosugi ....................... 378/197 |
| 6,382,833 B2 * | 5/2002 | Leandersson et al. ...... 378/197 |
| 6,412,978 B1 * | 7/2002 | Watanabe et al. .......... 378/197 |
| 6,428,206 B1 * | 8/2002 | Watanabe ................... 378/197 |

(Continued)

FOREIGN PATENT DOCUMENTS

JP 2-29238 1/1990

(Continued)

*Primary Examiner*—Allen C. Ho
(74) *Attorney, Agent, or Firm*—Oblon, Spivak, McClelland, Maier & Neustadt, L.L.P.

(57) ABSTRACT

A controller controls a floor-mounted rotary arm mounted at one end on a floor rotatably about a substantially vertical rotation axis, a stand supported at the other end of the floor-mounted rotary arm rotatably about a substantially vertical rotation axis, a substantially C-shaped arm supported by the stand, an X-ray tube supported at one end of the C-arm, and an X-ray detector supported at the other end of the C-arm rotatably about a shooting axis passing through the X-ray focus of the X-ray tube and the center of the detection surface. The controller includes the steps of moving the X-ray tube and the X-ray detector linearly by controlling the rotation of the floor-mounted rotary arm and the rotation of the stand, and maintaining the orientation of the image in a display screen by controlling the axial rotation of the X-ray detector in synchronization with the rotation of the floor-mounted rotary arm and the rotation of the stand.

14 Claims, 8 Drawing Sheets

U.S. PATENT DOCUMENTS 7,018,097 B2 * 3/2006 Schmitt ................. 378/197
7,261,464 B2 * 8/2007 Noda et al. ............. 378/197

FOREIGN PATENT DOCUMENTS

| JP | 9-70400 | 3/1997 |
| JP | 2000-70248 | 3/2000 |
| JP | 2003-250784 | 9/2003 |
| JP | 2006-192217 | 7/2006 |
| JP | 2006-239126 | 9/2006 |

\* cited by examiner

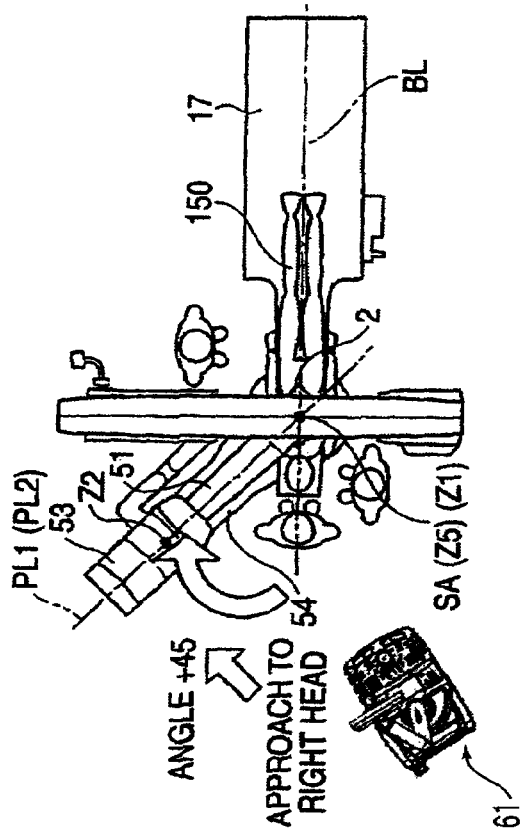
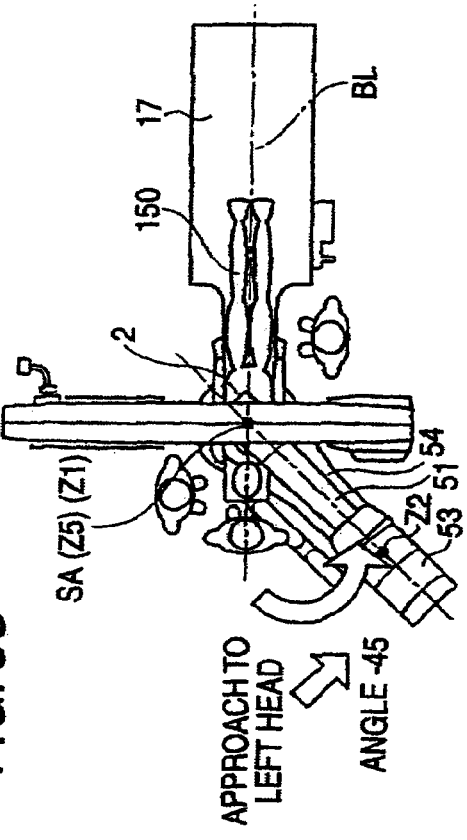
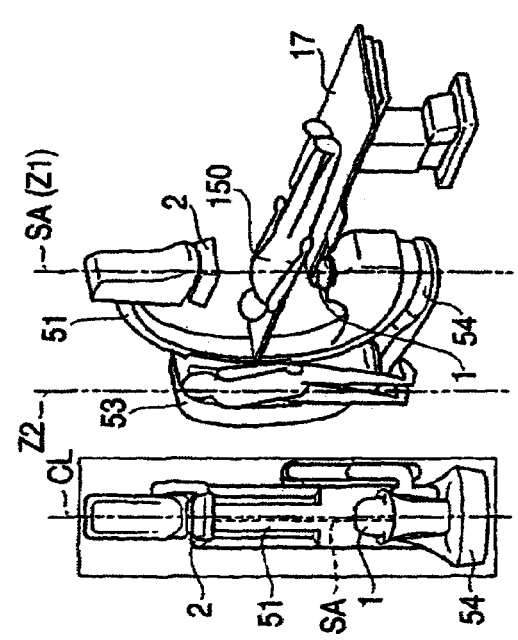
FIG. 5A
FIG. 5B
FIG. 5C

METHOD FOR CONTROLLING X-RAY DIAGNOSTIC APPARATUS

CROSS-REFERENCE TO RELATED APPLICATIONS

This is a Continuation Application of PCT Application No. PCT/JP2006/314588, filed Jul. 24, 2006, which was published under PCT Article 21(2) in Japanese.

BACKGROUND OF THE INVENTION

1. Field of the Invention

The present invention relates to a method for controlling an X-ray diagnostic apparatus having a floor-mounted C-arm.

2. Description of the Related Art

Medical imaging diagnostic technology using X-ray diagnostic apparatus, MRI apparatus, or X-ray CT scanners has made rapid progress with the advance of computer technology, and has become indispensable for today's medical treatment.

In recent years, X-ray diagnosis has made a progress mainly in the field of circulatory. organs with the advance of catheterization. X-ray diagnostic apparatuses for circulatory organs generally include an X-ray generator, an X-ray detector, a support unit for the X-ray generator and the X-ray detector, a table (tabletop), an image processor, a display, and so on. The support unit turns, rotates, or moves a C-arm or Ω-arm around a patient (hereinafter, referred to as a subject) to allow radiography imaging in an optimum position or direction An X-ray film or an image intensifier (II) has been used as X-ray detection element for use in the X-ray detector of X-ray diagnostic apparatuses. In the radiography imaging using the II, X-ray projection data (hereinafter, referred to as projection data) that is given by the passage of X-rays generated from an X-ray generator through the subject to an optical image by the II, and the optical image is converted to an electric signal by an X-ray TV camera, then converted from analog to digital data, and displayed on a monitor. Accordingly, the radiograph using the II allows real-time imaging which was impossible for that using a film, and also allows collection of digital projection data, thus allowing various image processing. As an alternative to the II, a two-dimensional-array plane detector has received attention, part of which has already come into practical use.

FIG. 9 shows a C-arm support unit used in a conventional circulatory-organ X-ray diagnostic apparatus. An X-ray generator 1101 is mounted to an end (the lower end) of a C-arm 1103 of the C-arm support unit 1110, while an X-ray detector 1102 having a plane detection element is mounted to the other end (the upper end) in such a manner as to face the X-ray generator 1101. The alternate long and short dash line 1108 in the drawing indicates an exposure axis connecting the focus of the X-ray tube in the X-ray generator 1101 and the center of the plane detection element of the X-ray detector 1102. The alternate long and short dash line indicates also the center line of a tabletop 1107 in a lateral reference position, or a base line BL for exposure which substantially agrees with the body axis of the subject.

The C-arm 1103 is retained by a stand 1105 installed on a floor 1106 through an arm holder 1104. The C-arm 1103 is mounted to an end of the arm holder 1104 slidably in the direction indicated by arrow a. The arm holder 1104 is mounted to the top of the stand 1105 in such a manner as to turn or rotate in the direction indicated by arrow b. The stand 1105 is composed of a stand fixing section 1105a fixed to the floor 1106 and a stand moving section 1105b that is rotatable in the direction of arrow c about the support axis.

The X-ray generator 1101 and the X-ray detector 1102 (hereinafter, collectively referred to as an imaging system) are set in a position and direction suitable for a subject (not shown) laid on the tabletop 1107 by the sliding of the C-arm 1103 in the direction a and the rotation of the arm holder 1104 in the direction b. Turning the stand moving section 1105b in the direction c enables the imaging system and the C-arm 1103 to be separated from the subject. The separation of the imaging system and the C-arm 1103 provides a working space for a doctor or a medical technologist (hereinafter, referred to as an operator) around the head of the subject, thus facilitating rearrangement of the subject on the tabletop 1107 or turn of the position before and after the examination, and placement of anesthetic equipment.

An L-shaped offset arm, as shown in FIG. 9, is generally used as the arm holder 1104. Forming the arm holder 1104 in L-shape enables the C-arm 1103 to be mounted on the side of the tabletop 1107, thus permitting the longitudinal end of the tabletop 1107 to be moved in the direction of arrow f to the vicinity of the stand 1105. In other words, the use of the L-shaped arm holder 1104 increases the moving range of the tabletop 1107, thereby increasing the subject distance. The use of the L-shaped arm holder 1104 also has the advantage of providing enough working space for the operator around the subject's head.

However, the provision of working space and increase of the subject distance by the rotation of the stand moving section 1105b or the L-shaped arm holder 1104 have limitation because the stand 1105 is fixed on the floor 1106, which is not always enough for the operator.

To solve the above problems, a ceiling-mounted C-arm support unit is proposed in which an arm holder is fixed to an end of an arm that is rotatably fixed at the other end to the ceiling, and in which the exposure region of the subject to can be set freely by bringing the rotation axis of the arm into agreement with the longitudinal center of the tabletop (for example, refer to JP-A-2000-70248).

BRIEF SUMMARY OF THE INVENTION

It is an object of the present invention to improve the operability of radiography in controlling an X-ray diagnostic apparatus having a floor C-arm.

According to an aspect of the invention, A method for controlling an X-ray diagnostic apparatus comprising a floor-mounted rotary arm mounted at one end on a floor rotatably about a substantially vertical rotation axis; a stand supported at the other end of the floor-mounted rotary arm rotatably about a substantially vertical rotation axis; a substantially C-shaped arm slidably supported by the stand; an X-ray tube supported at one end of the C-arm; an X-ray detector supported at the other end of the C-arm rotatably about a shooting axis passing through the X-ray focus of the X-ray tube and a center of the detection surface; and a controller for controlling the components of the apparatus, the method comprising the steps of: moving the X-ray tube and the X-ray detector linearly by controlling the rotation of the floor-mounted rotary arm and the rotation of the stand; and maintaining the orientation of the image in a display screen by controlling the axial rotation of the X-ray detector in synchronization with the rotation of the floor-mounted rotary arm and the rotation of the stand is provided.

BRIEF DESCRIPTION OF THE SEVERAL VIEWS OF THE DRAWING

FIG. 5A is a diagram showing a reference position controlled by the moving-mechanism drive controller of FIG. 3;

FIG. 5B is a diagram showing a right-head approach position controlled by the moving-mechanism drive controller of FIG. 3;

FIG. 5C is a diagram showing a left-head approach position controlled by the moving-mechanism drive controller of FIG. 3;

DETAILED DESCRIPTION OF THE INVENTION

Embodiments of the invention will be described with reference to the drawings.

Figure 1:
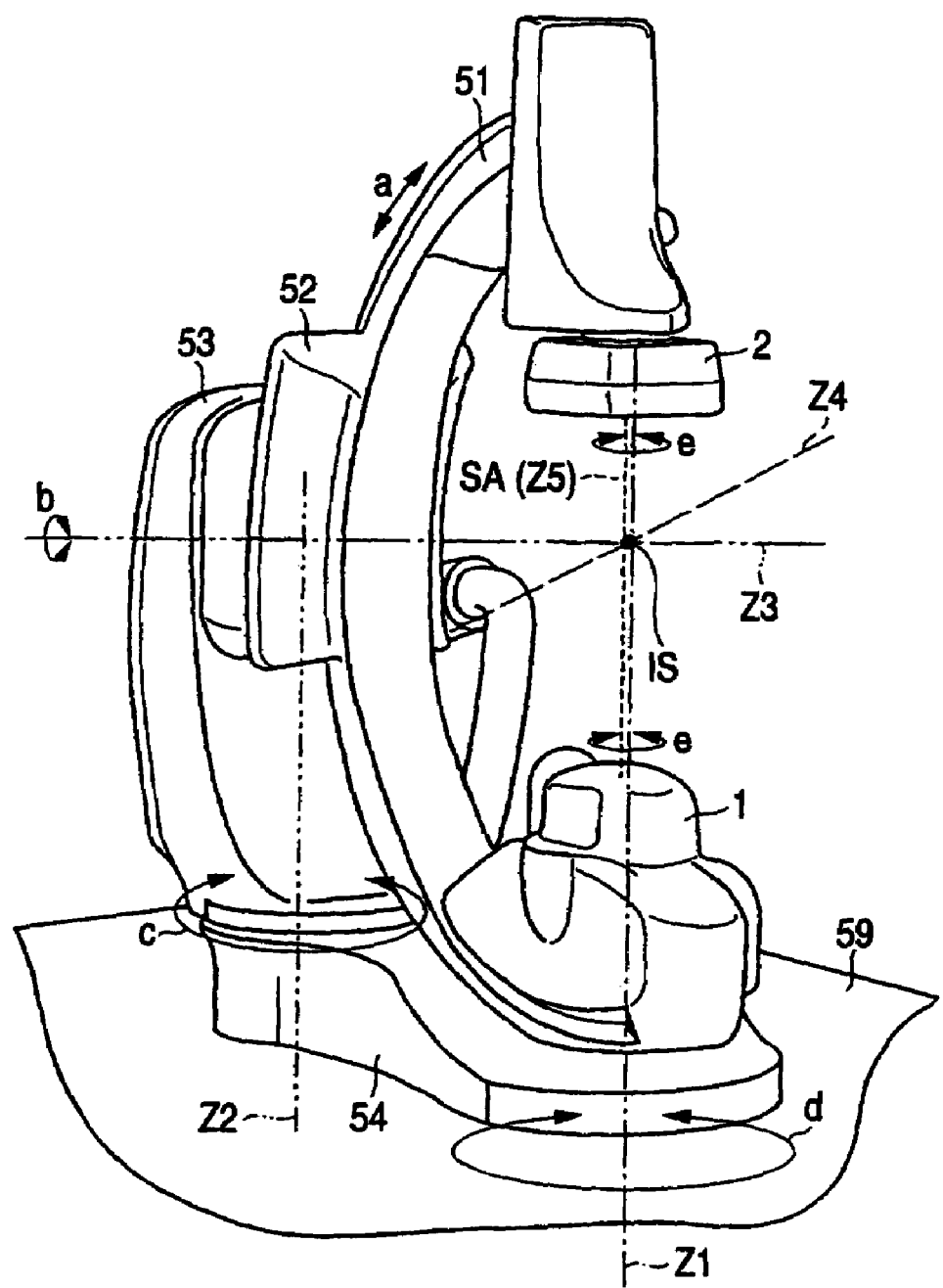
FIG. 1 is an external view of a C-arm support unit of an X-ray diagnostic system according to an embodiment of the invention.
Figure 2:
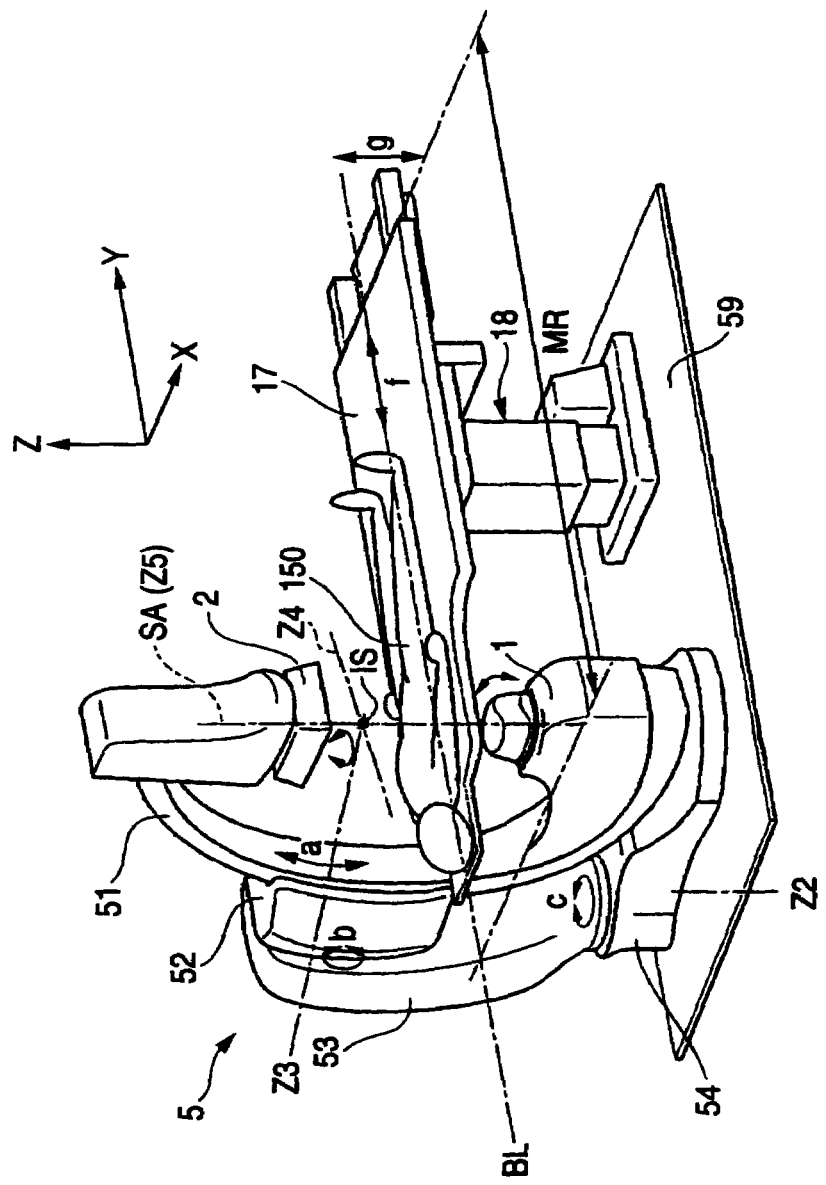
FIG. 2 is an external view of the C-arm support unit of the X-ray diagnostic system according to the embodiment of the invention.

Referring to FIGS. 1 and 2, a floor-mounted rotary arm 54 is mounted on a floor 59 in such a manner as to rotate (d) at on end about a substantially vertical first rotation axis Z1. The first rotation axis Z1 is a vertical axis orthogonal to a horizontal base line BL. During exposure, a subject 150 is laid on a tabletop 17 in such a manner that the body axis of the subject 150 substantially agrees with the base line BL. The base line BL substantially agrees with the center line of the tabletop 17. The tabletop 17 is disposed on a table 18 in such a manner as to be movable along the length parallel to the base line BL. The first rotation axis Z1 crosses the base line BL within the longitudinal moving range MR of the tabletop 17. That is, the floor-mounted rotary arm 54 is disposed in the longitudinal moving range MR.

A stand 53 is supported at the other end of the floor-mounted rotary arm 54 in such a manner as to be rotatable (c) about a substantially vertical second rotation axis Z2. The stand 53 supports an arm holder 52 in such a manner as to be rotatable (b) about a substantially horizontal third rotation axis (C-arm horizontal rotation axis) Z3. The arm holder 52 supports a substantially C-shaped arm 51 in such a manner as to be slidably rotatable (a) about a substantially horizontal fourth rotation axis (sliding rotation axis) Z4 orthogonal to the C-arm horizontal rotation axis Z3. A C-arm 51 is fitted at one end with an X-ray generator 1. The C-arm 51 has at the other end an X-ray detector (commonly referred to as a flat panel detector (FPD)) 2 which typically has a plurality of two-dimensional-array X-ray detecting semiconductor devices.

Referring to FIG. 5A, the X-ray generator 1 and the X-ray detector 2 are disposed with an offset of zero from the C-arm 51 so that the center line CL of the C-arm 51 agrees with the shooting axis SA connecting the X-ray focus of the X-ray tube and the center of the detection surface of the X-ray detector 2, that is, the shooting axis SA connecting the X-ray focus of the X-ray tube and the center of the detection surface of the X-ray detector 2 is located in the plane passing through the center line CL of the C-arm 51.

Although not shown, the X-ray generator 1 includes an X-ray tube and an X-ray limiting mechanism that forms the X-ray irradiation field into a desired shape such as a rectangle or a circle. The X-ray limiting mechanism is supported by an axial rotation mechanism 515-1 (see FIG. 3) in such a manner as to be rotatable about the shooting axis SA (in agreement with the fifth rotation axis Z5) connecting the X-ray focus of the X-ray tube and the center of the detection surface of the X-ray detector 2. Similarly, the X-ray detector 2 is supported by an axial rotation mechanism 515-2 in such a manner as to be rotatable about the shooting axis SA (in agreement with the fifth rotation axis Z5).

The apparatus is designed such that the shooting axis SA (Z5) passing through the X-ray focus of the X-ray generator 1 and the center of the detection surface of the X-ray detector 2 cross the C-arm horizontal rotation axis Z3 and the slide rotation axis Z4 at one point. As well known, the absolute coordinates of the intersection point (the position on the coordinate system of the exposure room) do not change unless the stand 53 turns on the second rotation axis Z2 even when the C-arm 51 rotates about the C-arm horizontal rotation axis Z3, even when the C-arm 51 rotates about the slide rotation axis Z4, or even when the floor-mounted rotary arm 54 rotates about the first rotation axis Z1. The absolute coordinates are generally called an isocenter IS.

Referring to FIG. 1, the apparatus is designed such that when the turning angle of the stand 53 about the second rotation axis Z2 is at the reference angle (0°), so that the C-arm 51 overlaps over the floor-mounted rotary arm 54 to the smallest, the isocenter is located on the first rotation axis Z1 of the floor-mounted rotary arm 54, in other words, such that the shooting axis SA (Z5), the C-arm horizontal rotation axis Z3, and the slide rotation axis Z4 intersect the first rotation axis Z1 of the floor-mounted rotary arm 54 on the isocenter. That is, the length of the floor-mounted rotary arm 54, the size of the stand 53, the size of the arm holder 52, and the radius of the C-arm 51 are totally determined so that the distance between the first rotation axis Z1 of the floor-mounted rotary arm 54 and the second rotation axis Z2 of the stand 53 and the distance between the second rotation axis Z2 of the stand 53 and the isocenter IS are the same.

With this design, when the rotation angle of the C-arm 51 about the C-arm horizontal rotation axis Z3 is at the reference angle (0°), and moreover, when the rotation angle of the C-arm 51 about the slide rotation axis Z4 is at the reference angle (0°), so that the shooting axis SA (Z5) is in the vertical direction, the shooting axis SA (Z5) substantially agrees with the first rotation axis Z1 of the floor-mounted rotary arm 54 in the case in which the turning angle of the stand 53 about the second rotation axis Z2 is at the reference angle (0°).

Figure 3:
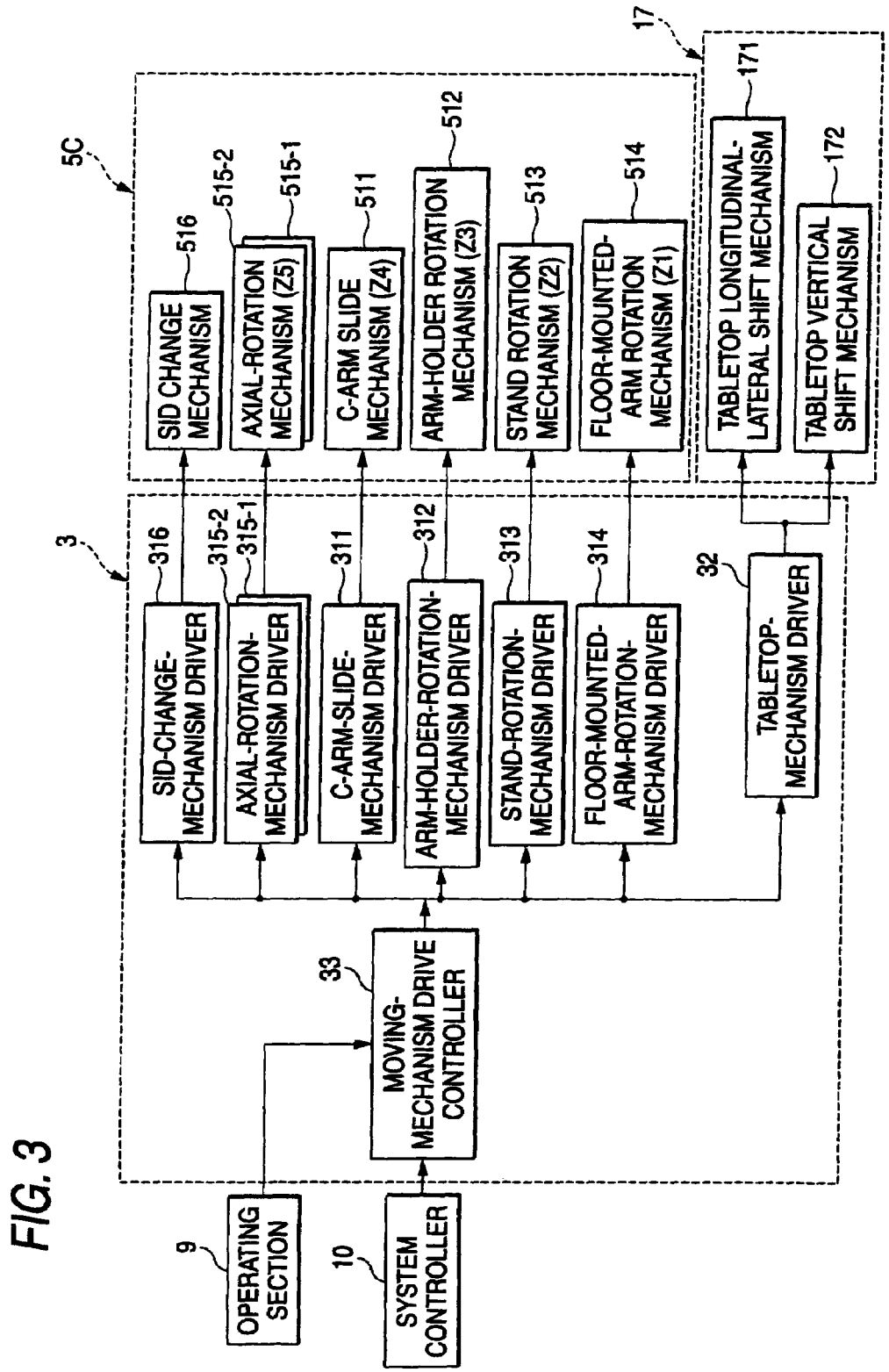
FIG. 3 is a functional block diagram of the principal part of the X-ray diagnostic system according to the embodiment of the invention.

Referring to FIG. 3, typically, driving signals are respectively supplied from drivers 311, 312, 313, 314, 315-1, 315-2, and 316 serving as power source to the motors of the mechanisms 511, 512, 513, 514, 515-1, 515-2, and 516 of a C-arm support unit 5 under the control of a moving-mechanism drive controller 33 of a moving-mechanism driver 3 in response to the control signals from a system controller 10 or operating signals from an operating section 9. Thus, the components are rotated or slid. Similarly, a driving signal is supplied from a tabletop-mechanism driver 32 to a longitudinal-lateral shift mechanism 171 and a vertical shift mechanism 172 of the tabletop 17 under the control of the moving-mechanism drive controller 33 of the moving-mechanism driver 3 in response to the control signal from a system controller 10 or the operating signal from the operating section 9. Thus, the brake of the tabletop 17 is released to be able to move in the longitudinal direction f (in the Y-direction) or in the lateral direction (in the X-direction), or the tabletop 17 can be moved in the vertical direction g.

Figure 4:
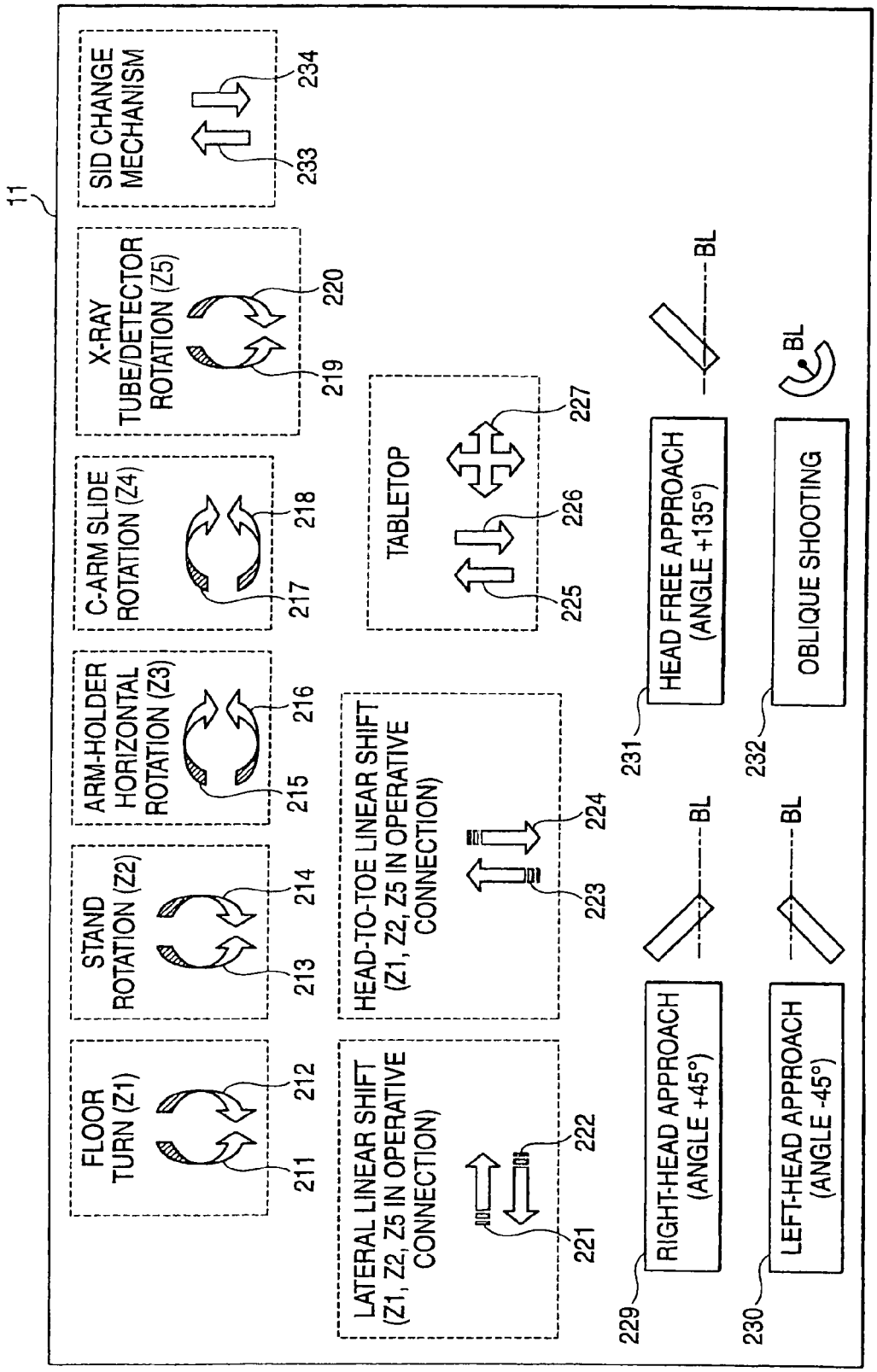
FIG. 4 is a diagram of an example of the operation screen of the operating section of FIG. 3.

FIG. 4 shows the operation screen of an operating section 11. The operation screen may be either a touch panel or an operator console in which substantial switches or buttons are arranged. The operation screen has manual operation buttons 211 to 227, 233, and 234 for manually controlling the movement of the components. The operation screen also has preset buttons 229, 230, 231, and 232 for automatically moving the C-arm support unit 5 in a predetermined position.

When the floor-mounted-arm turning button 211 is clicked or pressed, the controller 33 controls a driver 314 so that the floor-mounted rotary arm 54 is turned forward (counterclockwise) about the rotation axis Z1 by the floor-mounted-arm rotating mechanism 514 by an angle corresponding to the operation amount, typically, pressing time. When the floor-mounted-arm turning button 212 is clicked or pressed, the controller 33 controls the driver 314 so that the floor-mounted rotary arm 54 is turned backward (clockwise) about the rotation axis Z1 by the floor-mounted-arm rotating mechanism 514 by an angle corresponding to the operation amount.

When the stand turning button 213 is clicked or pressed, the controller 33 controls a driver 313 so that the stand 53 is turned forward (counterclockwise) about the rotation axis Z2 by the stand turning mechanism 513 by an angle corresponding to the operation amount. When the stand turning button 214 is clicked or pressed, the controller 33 controls the driver 313 so that the stand 53 is turned backward (clockwise) about the rotation axis Z2 by the stand turning mechanism 513 by an angle corresponding to the operation amount.

When the arm-holder horizontally turning button 215 is clicked or pressed, the controller 33 controls a driver 312 so that the arm holder 52 is turned forward horizontally about the rotation axis Z3 by the arm-holder turning mechanism 512 by an angle corresponding to the operation amount. When the arm-holder horizontally turning button 216 is clicked or pressed, the controller 33 controls the driver 312 so that the arm holder 52 is turned backward horizontally about the rotation axis Z3 by the arm-holder turning mechanism 512 by an angle corresponding to the operation amount.

When the C arm slide rotating button 217 is clicked or pressed, the controller 33 controls a driver 311 so that the C arm 51 is slid forward about the rotation axis Z4 and along the arm holder 52 by the C arm sliding mechanism 511 by an angle corresponding to the operation amount. When the C arm slide rotating button 218 is clicked or pressed, the controller 33 controls the driver 311 so that the C arm 51 is slid backward about the rotation axis Z4 and along the arm holder 52 by the C arm sliding mechanism 511 by an angle corresponding to the operation amount.

When the X-ray-tube/detector rotating button 219 is clicked or pressed, the controller 33 controls a driver 315-1 and 315-2 so that the X-ray limiting device rotates forward about the rotation axis Z5 (shooting axis SA) together with the X-ray detector 2 by an angle corresponding to the operation amount in synchronism with the axial rotation mechanisms 515-1 and 515-2. When the X-ray-tube/detector rotating button 220 is clicked or pressed, the controller 33 controls the driver 315-1 and 315-2 so that the X-ray limiting device rotates backward about the rotation axis Z5 (shooting axis SA) together with the X-ray detector 2 by an angle corresponding to the operation amount in synchronism with the axial rotation mechanisms 515-1 and 515-2.

When the tabletop operating button 225 is clicked or pressed, the controller 33 controls the driver 32 so that the tabletop 17 rises along a vertical axis by a distance corresponding to the operation amount by the vertically moving mechanism 172. When the tabletop operating button 226 is clicked or pressed, the controller 33 controls the driver 32 so that the tabletop 17 falls along the vertical axis by a distance corresponding to the operation amount by the vertically moving mechanism 172. When the tabletop brake button 227 is clicked or pressed, the brake is released to enable the tabletop 17 to be moved in the longitudinal direction (the Y-direction) or in the lateral direction (the X-direction). When the tabletop brake button 227 is clicked or pressed again after the tabletop is moved, the tabletop 17 is braked.

When the SID change button 233 is clicked or pressed, the controller 33 controls the SID change mechanism 516 so as to synchronously separate the X-ray tube 1 and the X-ray detector 2 from the isocenter IS along the shooting axis SA by a distance corresponding to the operation amount to increase the SID (the distance between the X-ray tube 1 and the X-ray detector 2). When the SID change button 234 is clicked or pressed, the controller 33 controls the SID change mechanism 516 so as to synchronously bring the X-ray tube 1 and the X-ray detector 2 close to the isocenter IS along the shooting axis SA by a distance corresponding to the operation amount to decrease the SID (the distance between the X-ray tube 1 and the X-ray detector 2).

Figure 7A:
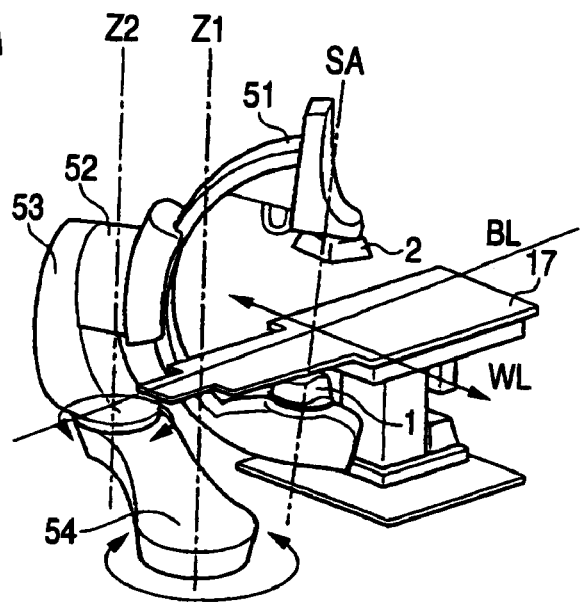
FIG. 7A is a diagram of the shift of a shooting axis achieved by the synchronous control of the moving-mechanism drive controller of FIG. 3.
Figure 7B:
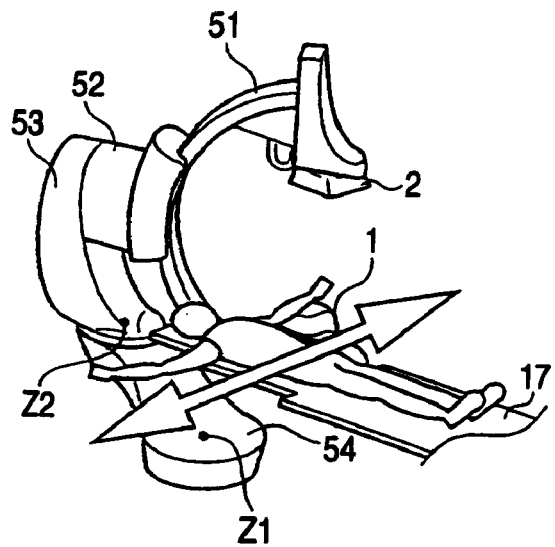
FIG. 7B is a diagram of the lateral shift of the shooting axis achieved by the synchronous control of the moving-mechanism drive controller of FIG. 3.

When the lateral linear shift button 221 is clicked or pressed, the controller 33 controls the drivers 314 and 313 so as to move the X-ray tube 1 and the X-ray detector 2 together with the C-arm 51 linearly substantially in parallel with the straight line WL in such a manner that the shooting axis SA shifts from initial position, shown in FIG. 7A, to the left by a distance corresponding to the operation amount while maintaining the intersection with the straight line WL orthogonal to the base line BL (see FIG. 7B). The controller 33 controls the rotation of the floor-mounted rotary arm 54 about the rotation axis Z1 and the turn of the stand 53 about the rotation axis Z2 so as to shift the shooting axis SA linearly. Actually, the relationship between the rotation angle of the floor-mounted rotary arm 54 and that of the stand 53 for locating the shooting axis SA on the straight line WL is determined in advance. The controller 33 individually controls the rotation of the floor-mounted rotary arm 54 and the turn of the stand 53 according to the relationship. Of course, the controller 33 may turn the stand 53 in connection with the rotation of the floor-mounted rotary arm 54 so as to locate the shooting axis SA on the straight line WL. The controller 33 may also rotate the floor-mounted rotary arm 54 in synchronization with the turn of the stand 53 so as to locate the shooting axis SA on the straight line WL. Although the floor-mounted rotary arm 54 and the stand 53 typically rotate at the same time, the floor-mounted rotary arm 54 and the stand 53 may be rotated alternately.

Furthermore, in order to prevent the turn of the image associated with the rotation of the floor-mounted rotary arm 54 about the rotation axis Z1 and the rotation of the stand 53 about the rotation axis Z2 and maintain the orientation of the image, the controller 33 controls the X-ray limiting device and the X-ray detector to rotate about the rotation axis Z5 (shooting axis SA) by the axial rotation mechanisms 515-1 and 515-2 in synchronism with the rotation of the floor-mounted rotary arm 54 about the rotation axis Z1 and the rotation of the stand 53 about the rotation axis Z2. Similarly, when the lateral linear shift button 222 is clicked or pressed, the controller 33 controls the drivers 314 and 313 so as to move the X-ray tube 1 and the X-ray detector 2 together with the C-arm 51 linearly substantially in parallel with the straight line WL in such a manner that the shooting axis SA shifts to the right by a distance corresponding to the operation amount while maintaining the intersection with the straight line WL. The controller 33 controls the rotation of the floor-mounted rotary arm 54 about the rotation axis Z1 and the turn of the stand 53 about the rotation axis Z2 so as to shift the shooting axis SA linearly. Actually, the relationship between the rotation angle of the floor-mounted rotary arm 54 and that of the stand 53 for locating the shooting axis SA on the straight line WL is determined in advance. The controller 33 individually controls the rotation of the floor-mounted rotary arm 54 and the turn of the stand 53 according to the relationship. Of course, the controller 33 may turn the stand 53 in connection with the rotation of the floor-mounted rotary arm 54 so as to locate the shooting axis SA on the straight line WL. The controller 33 may also rotate the floor-mounted rotary arm 54 in synchronization with the turn of the stand 53 so as to locate the shooting axis SA on the straight line WL. Although the floor-mounted rotary arm 54 and the stand 53 typically rotate at the same time, the floor-mounted rotary arm 54 and the stand 53 may be rotated alternately.

Furthermore, in order to prevent the turn of the image associated with the rotation of the floor-mounted rotary arm 54 about the rotation axis Z1 and the rotation of the stand 53 about the rotation axis Z2 to fix the orientation of the image, the controller 33 controls the X-ray limiting device and the X-ray detector to rotate about the rotation axis Z5 (shooting axis SA) by the axial rotation mechanisms 515-1 and 515-2 in synchronization with the rotation of the floor-mounted rotary arm 54 about the rotation axis Z1 and the rotation of the stand 53 about the rotation axis Z2.

Since the rotation of the floor-mounted rotary arm 54 and the rotation of the stand 53 are operatively associated, a wide coverage across the width of the patient can be provided even with the floor-fixed support unit. An example of the characteristic arrangements is a patient upper-arm position. The sequence to the position is as follows: the arm 51 is set in a patient's head position and moved in a desired right or left position by a manual/auto positioning operation. Specifically, the arm 54 is turned to thereby set the arm 51 in the patient's head position. The floor-mounted rotary arm 54 and the stand 53 are turned in association with each other to move the stand to the right or left. A possible motion of the arm 51 is to linearly move across the width of the patient by the interconnected turns of the floor-mounted rotary arm 54 and the stand 53 by one action of the button 221 or 222. The X-ray detector 2 and the X-ray limiting device are controlled so as to orient the image constantly, thus eliminating the need for manual setting. The rotation angles may be set manually at desired angles. An example of characteristic motions that can be made from the apparatus during examination/surgical operation after the arrangement is an approach from the upper arm. The increase in the lateral stroke allows the approach from the upper arm, the case of which is recently increasing. Since the X-ray limiting device and the X-ray detector 2 can be turned manually, unnecessary exposure when the arms are inclined can be prevented.

Figure 7C:
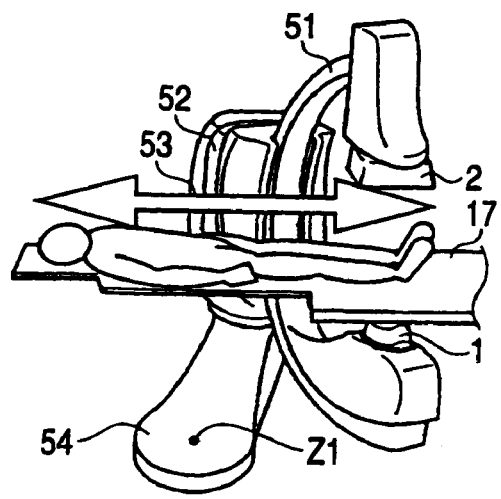
FIG. 7C is a diagram of the head-to-toe shift of the shooting axis achieved by the synchronous control of the moving-mechanism drive controller of FIG. 3.

When the head-to-toe linear shift button 223 is clicked or pressed, the controller 33 controls the drivers 314 and 313 so that the shooting axis SA shifts toward the head by a distance corresponding to the operation amount while maintaining the intersection with the base line BL to move the X-ray tube 1 and the X-ray detector 2 together with the C-arm 51 linearly substantially in parallel with the base line BL (see FIG. 7C). The controller 33 controls the rotation of the floor-mounted rotary arm 54 about the rotation axis Z1 and the rotation of the stand 53 about the rotation axis Z2 so as to shift the shooting axis SA linearly. Actually, the relationship between the rotation angle of the floor-mounted rotary arm 54 and that of the stand 53 for locating the shooting axis SA on the base line BL is determined in advance. The controller 33 individually controls the rotation of the floor-mounted rotary arm 54 and the rotation of the stand 53 according to the relationship. Of course, the controller 33 may turn the stand 53 in synchronization with the rotation of the floor-mounted rotary arm 54 so as to locate the shooting axis SA on the base line BL. The controller 33 may also rotate the floor-mounted rotary arm 54 in synchronization with the rotation of the stand 53 so as to locate the shooting axis SA on the base line BL. Although the floor-mounted rotary arm 54 and the stand 53 typically rotates at the same time, the floor-mounted rotary arm 54 and the stand 53 may be rotated alternately. The head-to-toe linear movement of the floor-mounted rotary arm 54 can be made on either side of the right and left of the subject. Which side the floor-mounted rotary arm 54 is disposed depends on the instruction of the operator.

Furthermore, in order to prevent the turn of the image associated with the rotation of the floor-mounted rotary arm 54 about the rotation axis Z1 and the rotation of the stand 53 about the rotation axis Z2 to fix the orientation of the image, the controller 33 controls the drivers 315-1 and 315-2 to turn the X-ray limiting device and the X-ray detector about the rotation axis ZS (shooting axis SA) by the axial rotation mechanisms 515-1 an 515-2 in synchronization with the rotation of the floor-mounted rotary arm 54 about the rotation axis Z1 and the rotation of the stand 53 about the rotation axis Z2.

When the head-to-toe linear shift button 224 is clicked or pressed, the controller 33 controls the drivers 314 and 313 so that the shooting axis SA shifts toward the toes by a distance corresponding to the operation amount while maintaining the intersection with the base line BL to move the X-ray tube 1 and the X-ray detector 2 together with the C-arm 51 linearly substantially in parallel with the base line BL. The controller 33 controls the rotation of the floor-mounted rotary arm 54 about the rotation axis Z1 and the rotation of the stand 53 about the rotation axis Z2 so as to shift the shooting axis SA linearly. Actually, the relationship between the rotation angle of the floor-mounted rotary arm 54 and that of the stand 53 for locating the shooting axis SA on the base line BL is determined in advance. The controller 33 individually controls the rotation of the floor-mounted rotary arm 54 and the rotation of the stand 53 according to the relationship. Of course, the controller 33 may turn the stand 53 in synchronization with the rotation of the floor-mounted rotary arm 54 so as to locate the shooting axis SA on the base line BL. The controller 33 may also rotate the floor-mounted rotary arm 54 in synchronization with the rotation of the stand 53 so as to locate the shooting axis SA on the base line BL. Although the floor-mounted rotary arm 54 and the stand 53 typically rotate at the same time, the floor-mounted rotary arm 54 and the stand 53 may be rotated alternately.

Furthermore, in order to prevent the turn of the image associated with the rotation of the floor-mounted rotary arm 54 about the rotation axis Z1 and the rotation of the stand 53 about the rotation axis Z2 to fix the orientation of the image, the controller 33 controls the drivers 315-1 and 315-2 to turn the X-ray limiting device and the X-ray detector about the rotation axis Z5 (shooting axis SA) by the axial rotation mechanisms 515-1 an 515-2 in synchronization with the rotation of the floor-mounted rotary arm 54 about the rotation axis Z1 and the rotation of the stand 53 about the rotation axis Z2.

Since the rotation of the floor-mounted rotary arm 54 and the rotation of the stand 53 are operatively associated, a wide coverage across the length of the patient can be provided even with the floor-fixed support unit. An example of the characteristic arrangements is a patient's leg position. The sequence to the position is as follows: the arm 51 is set in the patient's leg position by a manual/auto positioning operation. The floor-mounted rotary arm 54 is turned to the right or left of the patient. The floor-mounted rotary arm 54 and the stand 53 are turned in synchronization with each other to move the X-ray tube 1 and the X-ray detector 2 toward the legs. A possible motion of the arm 51 in this arrangement is to linearly move the X-ray tube 1 and the X-ray detector 2 across the length of the patient by the interconnected rotations of the floor-mounted rotary arm 54 and the stand 53 by one action of the button 223 or 224. This allows the examination or medical surgery of the whole body. This arrangement allows an arm motion in the direction, RAO/LAO or CRA/CAU, by one action of clinical angular control. The X-ray detector 2 and the X-ray limiting device are controlled so as to orient the image constantly, thus eliminating the need for manual setting. Examples of characteristic motions that can be made from the apparatus during examination/surgical operation after the arrangement include longitudinal scanning and digital subtraction angiography (DSA) of legs only by arm operation without moving the table. Retracting the arm 51 to the patient's toes as much as possible to clear the surrounding of the patient allows compatibility with surgical operation that needs no radiography. So, this apparatus can respond to a child's (pediatric) case, in this case occur that an operation change to another operation under a surgical operation, or plural operations are performed at once.

When the right-head-approach position button 229 is clicked or pressed, the controller 33 controls the drivers 313 and 314 so that the C-arm support unit 5 is set in a predetermined position suitable for increasing the work space for the operator to approach the subject 150 from the right head, as shown in FIGS. 5A and 5B. Specifically, since the stand 53 is turned to the reference position, the C-arm 51 comes over the floor-mounted rotary arm 54. That is, a second position line PL2 connecting the second rotation axis Z2 and the fifth rotation axis Z5 (shooting axis SA) agrees with a first position line PL1 connecting the first rotation axis Z1 and the second rotation axis Z2. Therefore, the fifth rotation axis Z5 (shooting axis SA) of the X-ray limiting device and the X-ray detector 2 substantially agrees with the first rotation axis Z1 of the floor-mounted rotary arm 54. Furthermore, the first and second position lines PL1 and PL2 are inclined positively substantially at 45 degrees with respect to the base line BL. The controller 33 controls the driver 314 to rotate the floor-mounted rotary arm 54 about the first rotation axis Z1 with the stand 53 at zero degree about the second rotation axis Z2 so as to have such a preset position. This position provides a wide work space sufficient for the operator to approach the right head of the subject 150. Further, diagnostic ultrasound apparatus 61 can be arranged in the right head area of the subject 150.

The position is automatically set by the operation of the right-head-approach position button 229, allowing quick shift to the position. The inclination angle is finely controlled by the manual operation with the button 211 or 212 as necessary. The controller 33 controls the orientation of the image according to the rotation of the X-ray detector 2 (FPD) and the X-ray limiting device. The preset angle can be changed as appropriate by setting.

When the left-head-approach position button 230 is clicked or pressed, the controller 33 controls the drivers 313 and 314 so that the C-arm support unit 5 is set in a predetermined position suitable for increasing the work space for the operator to approach the subject 150 from the left head, as shown in FIGS. 5A and 5C. Specifically, similarly to the right-head approach position, the C-arm 51 comes over the floor-mounted rotary arm 54 to make the shooting axis Z5 substantially agree with the rotation axis Z1. Furthermore, the first and second position lines PL1 and PL2 are inclined negatively substantially at 45 degrees with respect to the base line BL. The controller 33 controls the driver 314 to rotate the floor-mounted rotary arm 54 about the first rotation axis Z1 with the stand 53 at zero degree about the second rotation axis Z2 so as to have such a preset position. This position provides a wide work space sufficient for the operator to approach the left head of the subject 150. The position is automatically set by the operation of the left-head-approach position button 230, allowing quick shift to the position. The inclination angle is finely controlled by the manual operation with the button 211 or 212 as necessary. The controller 33 controls the orientation of the image according to the rotation of the X-ray detector 2 (FPD) and the X-ray limiting device. The preset angle can be changed as appropriate by setting.

Figure 6A:
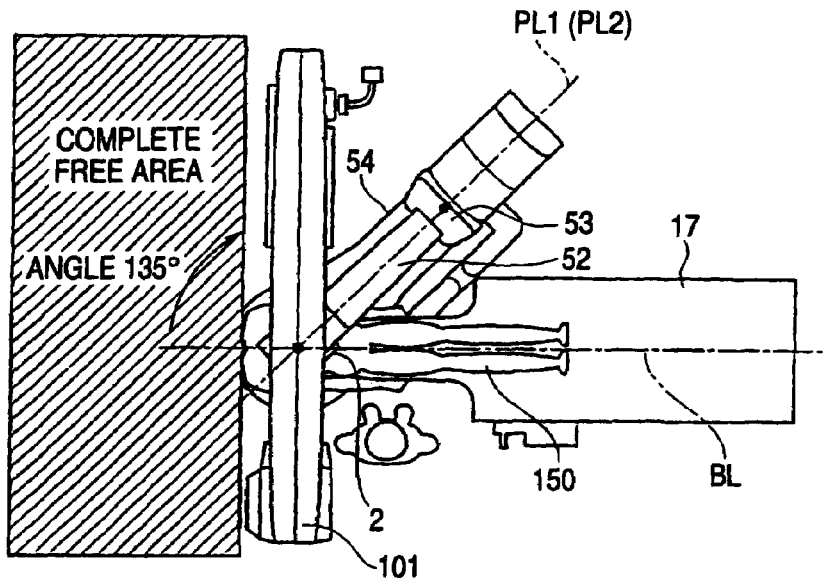
FIG. 6A is a plan view of a head free approach position controlled by the moving-mechanism drive controller of FIG. 3.
Figure 6B:
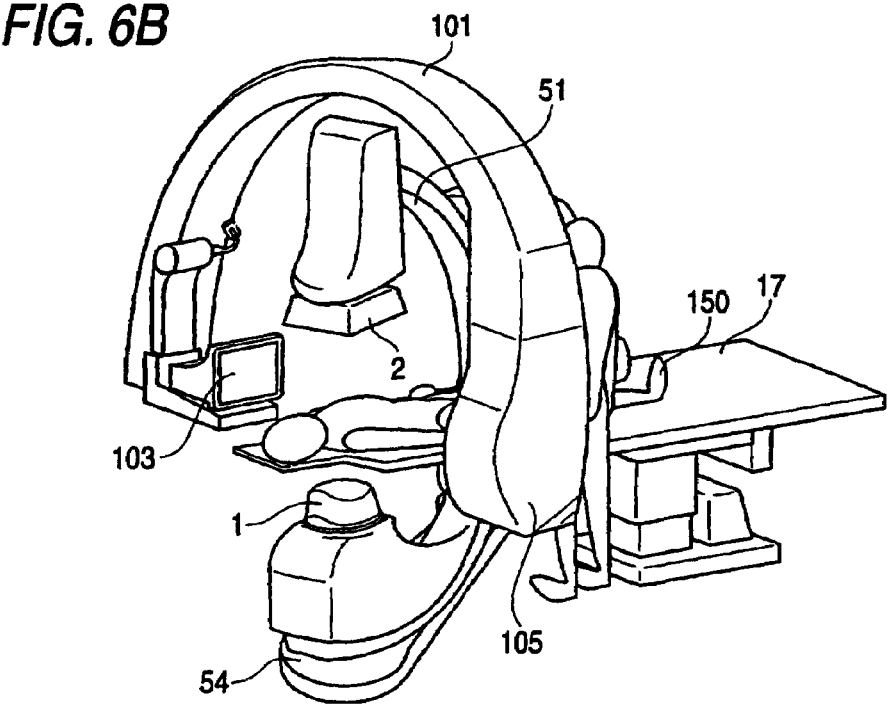
FIG. 6B is a perspective view of the head free approach position controlled by the moving-mechanism drive controller of FIG. 3.

When the head-free-approach position button 231 is clicked or pressed, the controller 33 controls the drivers 313 and 314 so that the C-arm support unit 5 is set in a predetermined position suitable for increasing the work space for the operator to approach the subject 150 from all around the head, as shown in FIGS. 6A and 6B. The position in which the work space is provided all around the head is typically advantageous for biplane imaging in combination with a ceiling-mounted Ω-arm 101 having an X-ray generator 105 and an X-ray detector 103 at both horizontal ends, respectively.

Specifically, similarly to the right-head approach position, the C-arm 51 comes over the floor-mounted rotary arm 51. Furthermore, the first and second position lines PL1 and PL2 are inclined positively or negatively substantially at 135 degrees with respect to the base line BL. The controller 33 controls the driver 314 to rotate the floor-mounted rotary arm 54 about the first rotation axis Z1 with the stand 53 at zero degree about the second rotation axis Z2 so as to have such a preset position. This position provides a wide work space sufficient for the operator to approach all around the head of the subject 150. The position is automatically set by the operation of the head-free-approach position button 231, allowing quick shift to the position. The inclination angle is finely controlled by the manual operation with the button 211 or 212 as necessary. The controller 33 controls the orientation of the image according to the rotation of the X-ray detector 2 (FPD) and the X-ray limiting device. The preset angle can be changed as appropriate by setting.

This rotation of the C-arm 51 between the Ω-arm 101 and the tabletop 17 during biplane imaging clears the vicinity of the head completely. An example of the characteristic arrangements is a biplane complete head free position. The sequence to the position is as follows: the Ω-arm 101 is moved to a retracted position; the Ω-arm 101 is then rotated on the floor into a position about 110 degrees or more to the left from the patient. Then, the Ω-arm 101 is moved from the retracted position to the biplane set position. When the operator is on the left of the patient, the C-arm 51 is moved to the right symmetric position. This position allows an arm motion in the direction, RAO/LAO or CRA/CAU, by one action of clinical angular control, and synchronous operation of the C-arm 51 and the Ω-arm 101. The X-ray detector 2 and the X-ray limiting device are controlled so as to orient the image constantly, thus eliminating the need for manual setting. This arrangement enables the periphery of the head to be completely cleared, thus having an advantage in installing an ultrasonic diagnostic apparatus or a general anesthetic apparatus and making an approach to the right and left carotid arteries during examination/surgical operation after arrangement and facilitating patient access of medical staff. This arrangement also provides the same operability and angles as normal biplane setting. Switching to surgical operation for brain cases can be made only by moving the tabletop 17 in the longitudinal direction.

Figure 8:
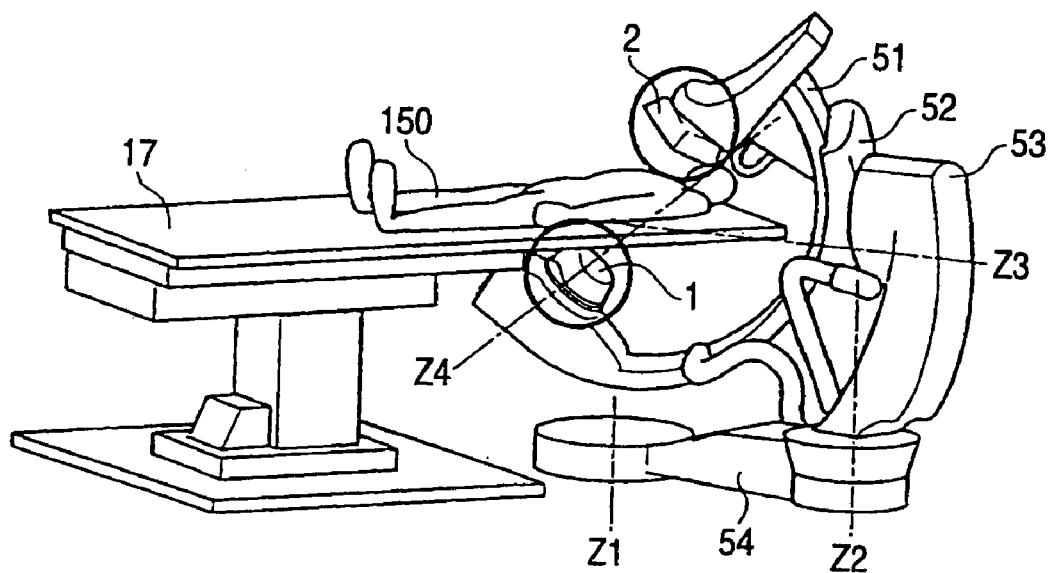
FIG. 8 is a diagram of an oblique exposure position controlled by the moving-mechanism drive controller of FIG. 3.
Figure 9:
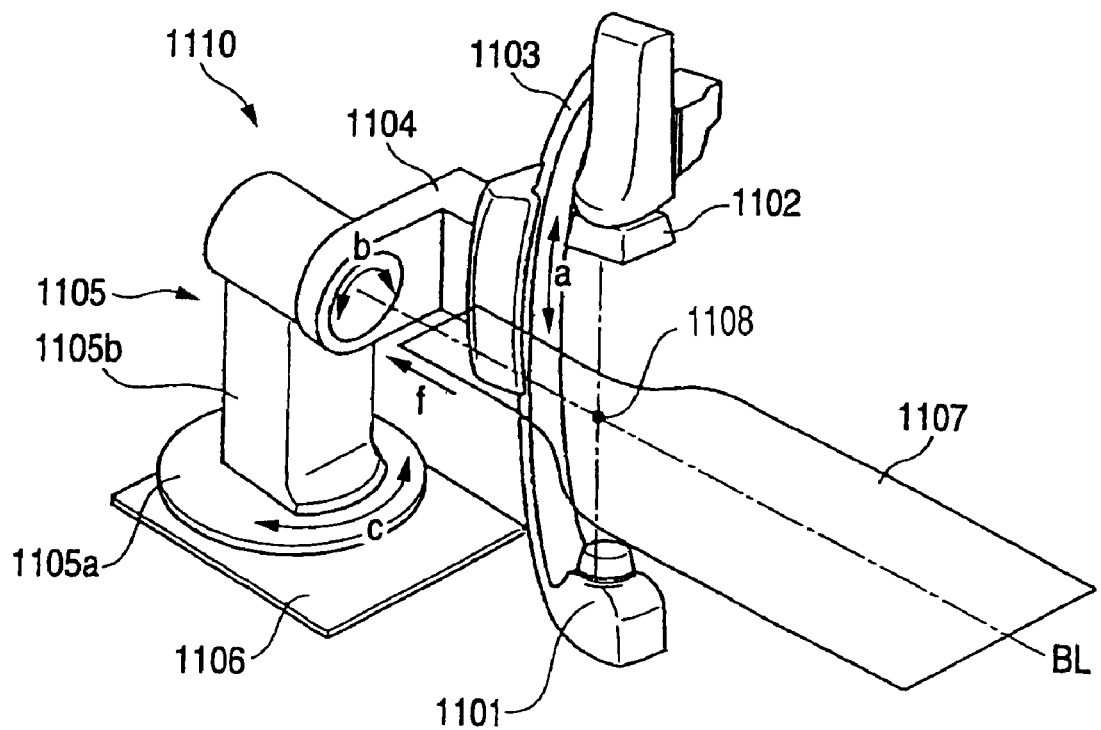
FIG. 9 is an external view of a floor-mounted C-arm support unit of a related art.

When the oblique exposing position button 232 is clicked or pressed, the controller 33 controls the driver 311 so that the C-arm support unit 5 is set in a position (in which the subject 150 is imaged in a slanting direction from between the front and the side) suitable for inserting the subject 150 from the head into an exposure region, as shown in FIG. 8. Specifically, the second position line PL2 connecting the second rotation axis Z2 and the fifth rotation axis Z5 (shooting axis SA) agrees with the first position line PL1 connecting the first rotation axis Z1 and the second rotation axis Z2, so that the C-arm 51 is placed over the floor-mounted rotary arm 51. The C-arm 51 rotates about the rotation axis Z4 and the rotation axis Z3 at predetermined angles, respectively, so that the shooting axis SA obliquely crosses the base line BL. At the same time, the X-ray limiting device and the X-ray detector 2 are rotated at a predetermined angle about the rotation axis Z5, thereby allowing the image to be oriented appropriately. Also for oblique exposure, a sufficient wide work space and a head position can be provided. The position is automatically set by the operation with the position button 232, allowing quick shift to the position. The inclination angle is finely controlled by the manual operation with the buttons 211 to 218 as necessary.

There is no need to provide the dedicated buttons 229, 230, 231, and 232; alternatively, a ten-key pad may be used to read numbers stored in advance.

It is to be understood that the invention is not limited to the embodiments and that various modifications may be made without departing from the spirit and scope thereof. It is to be further understood that the invention may be variously modified in appropriate combinations of the components of the embodiments. For example, several components may be omitted from all the components of the embodiments. Furthermore, the components of the different embodiments may be combined as appropriate.

The invention can improve the operability of radiography imaging in a method for controlling an X-ray diagnostic apparatus having a floor-mounted C-arm.

What is claimed is:

1. A method for controlling an X-ray diagnostic apparatus comprising a floor-mounted rotary arm mounted at one end on a floor rotatably about a substantially vertical rotation axis; a stand supported at the other end of the floor-mounted rotary arm rotatably about a substantially vertical rotation axis; a substantially C-shaped arm slidably supported by the stand; an X-ray tube supported at one end of the C arm; an X-ray detector supported at the other end of the C arm rotatably about a shooting axis passing through an X-ray focus of the X-ray tube and a center of the detection surface; a display screen and a controller, the method comprising the steps of:
   moving the X-ray tube and the X-ray detector linearly by controlling rotation of the floor-mounted rotary arm and rotation of the stand; and
   maintaining the orientation of an image in the display screen by controlling axial rotation of the X-ray detector in synchronization with the rotation of the floor-mounted rotary arm and the rotation of the stand.

2. The method for controlling the X-ray diagnostic apparatus according to claim 1, wherein the shooting axis can be made to substantially agree with a center line of the floor-mounted rotary arm.

3. The method for controlling the X-ray diagnostic apparatus according to claim 1, further comprising the step of controlling the rotation of the stand so that the shooting axis substantially agrees with a center line of the floor-mounted rotary arm according to an instruction of a specific operator.

4. A method for controlling an X-ray diagnostic apparatus comprising a floor-mounted rotary arm mounted at one end on a floor rotatably about a substantially vertical rotation axis; a stand supported at the other end of the floor-mounted rotary arm rotatably about a substantially vertical rotation axis; a substantially C-shaped arm slidably supported by the stand; an X-ray tube supported at one end of the C arm; an X-ray detector supported at the other end of the C arm rotatably about a shooting axis passing through an X-ray focus of the X-ray tube and a center of the detection surface; a display screen and a controller, the method comprising the steps of:
   controlling rotation of the floor-mounted rotary arm;
   moving the X-ray tube and the X-ray detector linearly by controlling rotation of the stand in synchronization with the rotation of the floor-mounted rotary arm; and
   maintaining the orientation of an image in the display screen by controlling axial rotation of the X-ray detector in synchronization with the rotation of the floor-mounted rotary arm.

5. A method for controlling an X-ray diagnostic apparatus comprising a floor-mounted rotary arm mounted at one end on a floor rotatably about a substantially vertical rotation axis; a stand supported at the other end of the floor-mounted rotary arm rotatably about a substantially vertical rotation axis; a substantially C-shaped arm slidably supported by the stand; an X-ray tube supported at one end of the C arm; an X-ray detector supported at the other end of the C arm rotatably about a shooting axis passing through an X-ray focus of the X-ray tube and a center of the detection surface; a display screen and a controller, the method comprising the steps of:
   controlling rotation of the stand;
   moving the X-ray tube and the X-ray detector linearly by controlling rotation of the floor-mounted rotary arm in synchronization with the rotation of the stand; and
   maintaining the orientation of an image in the display screen by controlling axial rotation of the X-ray detector in synchronization with the rotation of the stand.

6. A method for controlling an X-ray diagnostic apparatus comprising: a tabletop movably supported along a reference line; a floor-mounted rotary arm mounted at one end on a floor rotatably about a substantially vertical first rotation axis intersecting the reference line within the movable range of the tabletop; a driver of the rotation of the floor-mounted rotary arm; a stand supported at the other end of the floor-mounted rotary arm rotatably about a substantially vertical second rotation axis; a driver of the rotation of the stand; a substantially C-shaped arm supported by the stand; an X-ray tube supported at one end of the C arm; an X-ray detector supported at the other end of the C arm rotatably about a third rotation axis that substantially agrees with a shooting axis passing through an X-ray focus of the X-ray tube and a center of the detection surface; a driver of the rotation of the X-ray detector; a display screen and a controller, the method comprising the steps of:

moving the X-ray tube and the X-ray detector linearly substantially in parallel with the reference line by controlling the floor-mounted-rotary-arm rotation driver and the stand rotation driver; and rotating the X-ray detector in synchronization with rotation of the floor-mounted rotary arm and rotation of the stand by controlling the X-ray-detector rotation driver in such a manner as to maintain the orientation of an image in the display screen.

7. The method for controlling the X-ray diagnostic apparatus according to claim 6, wherein the X-ray diagnostic apparatus further comprises an X-ray limiting device provided to the X-ray tube rotatably about the third rotation axis and a driver of the rotation of the X-ray limiting device, the method further comprising the step of:

rotating the X-ray limiting device together with the X-ray detector by controlling the driver of the rotation of the X-ray limiting device.

8. A method for controlling an X-ray diagnostic apparatus comprising: a tabletop movably supported along a reference line; a floor-mounted rotary arm mounted at one end on a floor rotatably about a substantially vertical first rotation axis intersecting the reference line within the movable range of the tabletop; a driver of the rotation of the floor-mounted rotary arm; a stand supported at the other end of the floor-mounted rotary arm rotatably about a substantially vertical second rotation axis; a driver of the rotation of the stand; a substantially C-shaped arm supported by the stand; an X-ray tube supported at one end of the C arm; an X-ray detector for forming an image, the X-ray detector being supported at the other end of the C arm rotatably about a third rotation axis that substantially agrees with a shooting axis passing through an X-ray focus of the X-ray tube and a center of the detection surface; a driver of the rotation of the X-ray detector; a display screen and a controller, the method comprising the steps of:

rotating the floor-mounted rotary arm about the first rotation axis by controlling the driver of the rotation of the floor-mounted rotary arm;

rotating the stand about the second rotation axis in synchronization with the rotation of the floor-mounted rotary arm in such a manner as to move the X-ray tube and the X-ray detector linearly substantially in parallel with the reference line by controlling the stand rotation driver; and rotating the X-ray detector in synchronization with the rotation of the floor-mounted rotary arm and the rotation of the stand in such a manner as to maintain the orientation of the image in the display screen by controlling the X-ray-detector rotation driver.

9. A method for controlling an X-ray diagnostic apparatus comprising: a tabletop movably supported along a reference line; a floor-mounted rotary arm mounted at one end on a floor rotatably about a substantially vertical first rotation axis intersecting the reference line within the movable range of the tabletop; a driver of the rotation of the floor-mounted rotary arm; a stand supported at the other end of the floor-mounted rotary arm rotatably about a substantially vertical second rotation axis; a driver of the rotation of the stand; a substantially C-shaped arm supported by the stand; an X-ray tube supported at one end of the C arm; an X-ray detector supported at the other end of the C arm rotatably about a third rotation axis that substantially agrees with a shooting axis passing through an X-ray focus of the X-ray tube and a center of the detection surface; a driver of the rotation of the X-ray detector; a display screen and a controller, the method comprising the steps of:

rotating the stand about the second rotation axis by controlling the stand rotation driver;

rotating the floor-mounted rotary arm about the first rotation axis in synchronization with the rotation of the stand in such a manner as to move the X-ray tube and the X-ray detector linearly substantially in parallel with the reference line by controlling the driver of the rotation of the floor-mounted rotary arm; and rotating the X-ray detector in synchronization with the rotation of the floor-mounted rotary arm and the rotation of the stand in such a manner as to maintain the orientation of an image in the display screen by controlling the X-ray-detector rotation driver.

10. A method for controlling an X-ray diagnostic apparatus comprising: a tabletop movably supported along a reference line; a floor-mounted rotary arm mounted at one end on a floor rotatably about a substantially vertical first rotation axis intersecting the reference line within the movable range of the tabletop; a driver of the rotation of the floor-mounted rotary arm; a stand supported at the other end of the floor-mounted rotary arm rotatably about a substantially vertical second rotation axis; a driver of the rotation of the stand; a substantially C-shaped arm supported by the stand; an X-ray tube supported at one end of the C arm; an X-ray detector supported at the other end of the C arm rotatably about a third rotation axis that substantially agrees with a shooting axis passing through an X-ray focus of the X-ray tube and a center of the detection surface; a driver of the rotation of the X-ray detector; a display screen and a controller, the method comprising the steps of:

rotating the floor-mounted rotary arm about the first rotation axis and rotating the stand about the second rotation axis in such a manner as to move the shooting axis while maintaining an intersection with the reference line by controlling the driver of the rotation of the floor-mounted rotary arm and the stand rotation driver; and rotating the X-ray detector in synchronization with the rotation of the floor-mounted rotary arm and the rotation of the stand in such a manner as to maintain the orientation of an image in the display screen by controlling the X-ray-detector rotation driver.

11. A method for controlling an X-ray diagnostic apparatus comprising: a tabletop movably supported along a reference line; a floor-mounted rotary arm mounted at one end on a floor rotatably about a substantially vertical first rotation axis intersecting the reference line within the movable range of the tabletop; a driver of the rotation of the floor-mounted rotary arm; a stand supported at the other end of the floor-mounted rotary arm rotatably about a substantially vertical second rotation axis; a driver of the rotation of the stand; a substantially C-shaped arm supported by the stand; an X-ray tube supported at one end of the C arm; an X-ray detector for forming an image supported at the other end of the C arm rotatably about a third rotation axis that substantially agrees with a shooting axis passing through an X-ray focus of the X-ray tube and a center of the detection surface; a driver of the rotation of the X-ray detector; a display screen and a controller, the method comprising the steps of:
rotating the floor-mounted rotary arm about a first rotation axis and rotating the stand about a second rotation axis in such a manner as to move the X-ray tube and the X-ray detector linearly in a direction substantially orthogonal to the reference line by controlling the driver of the rotation of the floor-mounted rotary arm and the stand rotation driver; and
rotating the X-ray detector in synchronization with the rotation of the floor-mounted rotary arm and the rotation of the stand in such a manner as to maintain the orientation of the image in the display screen by controlling the X-ray-detector rotation driver.

12. A method for controlling an X-ray diagnostic apparatus comprising: a tabletop movably supported along a reference line; a floor-mounted rotary arm mounted at one end on a floor rotatably about a substantially vertical first rotation axis intersecting the reference line within the movable range of the tabletop; a driver of the rotation of the floor-mounted rotary arm; a stand supported at the other end of the floor-mounted rotary arm rotatably about a substantially vertical second rotation axis; a driver of the rotation of the stand; a substantially C-shaped arm supported by the stand; an X-ray tube supported at one end of the C arm; an X-ray detector for forming an image, the X-ray detector being supported at the other end of the C arm rotatably about a third rotation axis that substantially agrees with a shooting axis passing through an X-ray focus of the X-ray tube and a center of the detection surface; a driver of the rotation of the X-ray detector; a display screen and a controller, the method comprising the steps of:
rotating the floor-mounted rotary arm about the first rotation axis by controlling the driver of the rotation of the floor-mounted rotary arm; and
rotating the stand about the second rotation axis in synchronization with the rotation of the floor-mounted rotary arm in such a manner as to move the X-ray tube and the X-ray detector linearly in a direction substantially orthogonal to the reference line by controlling the stand rotation driver; and
rotating the X-ray detector in synchronization with the rotation of the floor-mounted rotary arm and the rotation of the stand in such a manner as to maintain the orientation of the image on the display screen by controlling the X-ray-detector rotation driver.

13. A method for controlling an X-ray diagnostic apparatus comprising: a tabletop movably supported along a reference line; a floor-mounted rotary arm mounted at one end on a floor rotatably about a substantially vertical first rotation axis intersecting the reference line within the movable range of the tabletop; a driver of the rotation of the floor-mounted rotary arm; a stand supported at the other end of the floor-mounted rotary arm rotatably about a substantially vertical second rotation axis; a driver of the rotation of the stand; a substantially C-shaped arm supported by the stand; an X-ray tube supported at one end of the C arm; an X-ray detector for forming an image supported at the other end of the C arm rotatably about a third rotation axis that substantially agrees with a shooting axis passing through an X-ray focus of the X-ray tube and a center of the detection surface; a driver of the rotation of the X-ray detector; a display screen and a controller, the method comprising the steps of:
rotating the stand about the second rotation axis by controlling the stand rotation driver;
rotating the floor-mounted rotary arm about the first rotation axis in synchronization with the rotation of the stand in such a manner as to move the X-ray tube and the X-ray detector linearly in a direction substantially orthogonal to the reference line by controlling the driver of the rotation of the floor-mounted rotary arm; and
rotating the X-ray detector in synchronization with the rotation of the floor-mounted rotary arm and the rotation of the stand in such a manner as to maintain the orientation of the image on the display screen by controlling the X-ray-detector rotation driver.

14. A method for controlling an X-ray diagnostic apparatus comprising: a tabletop movably supported along a reference line; a floor-mounted rotary arm mounted at one end on a floor rotatably about a substantially vertical first rotation axis intersecting the reference line within the movable range of the tabletop; a driver of the rotation of the floor-mounted rotary arm; a stand supported at the other end of the floor-mounted rotary arm rotatably about a substantially vertical second rotation axis; a driver of the rotation of the stand; a substantially C-shaped arm supported by the stand; an X-ray tube supported at one end of the C arm; an X-ray detector for forming an image supported at the other end of the C arm rotatably about a third rotation axis that substantially agrees with a shooting axis passing through an X-ray focus of the X-ray tube and a center of the detection surface; a driver of the rotation of the X-ray detector; a display screen and a controller, the method comprising the steps of:
rotating the floor-mounted rotary arm about the first rotation axis in such a manner that the floor-mounted rotary arm obliquely intersects the reference line at a specified angle by controlling the driver of the rotation of the floor-mounted rotary arm;
rotating the stand about the second rotation axis in such a manner that the third rotation axis substantially agrees with the first rotation axis by controlling the stand rotation driver; and
rotating the X-ray detector in such a manner as to maintain the orientation of the image on the display screen by controlling the X-ray-detector rotation driver.

* * * * *